United States Patent [19]

Fushimi et al.

[11] Patent Number: 5,661,003
[45] Date of Patent: Aug. 26, 1997

[54] WATER CHANNEL

[75] Inventors: Kiyohide Fushimi; Shinichi Uchida; Sei Sasaki, all of Tokyo; Fumiaki Marumo, 8-2-19 Tamagawa-gakuen, Machida, all of Japan

[73] Assignee: Fumiaki Marumo, Machida, Japan

[21] Appl. No.: 447,554

[22] Filed: May 23, 1995

Related U.S. Application Data

[63] Continuation of Ser. No. 126,365, Sep. 24, 1993, abandoned.

[30] Foreign Application Priority Data

Sep. 25, 1992 [JP] Japan .................................. 4-279157
Dec. 25, 1992 [JP] Japan .................................. 4-357838

[51] Int. Cl.$^6$ .......................... C07K 11/00; C07K 1/04; C12N 15/00; A61K 9/127
[52] U.S. Cl. .................. 435/69.1; 424/450; 435/71.2; 435/172.3; 435/252.3; 435/252.33; 435/254.11; 435/320.1; 435/365; 530/350
[58] Field of Search .................. 435/69.1, 71.2, 435/172.3, 240.2, 252.3, 252.33, 254.11, 320.1; 530/350; 424/450

[56] References Cited

PUBLICATIONS

Yamamoto, T. et al., "Vasopressin increases AQP–CD water channel in apical membrane of collecting duct cells in Brattleboro rats," *The American Physiological Society* (1995) Rapid Communication:C1546–1551.
Nielsen, S. et al., "Vasopressin increases water permeability of kidney collecting duct by inducing translocation of aquaporin–CD water channels to plasma membrane," *Proc. Natl. Acad. Sci. USA* (Feb. 1995) 92:1013–1017.
Deen, P.M.T. et al., "Requirement of Human Renal Water Channel Aquaporin–2 for Vasopressin–Dependent Concentration of Urine," *Science* (1 Apr. 1994) 264:92–95.
Echevarria, M. et al., "Expression of Multiple Water Channel Activities in *Xenopus Oocytes* Injected with mRNA from Rat Kidney," *The Journal of General Physiology* (1993) 101:827–841.
Fushimi, K. et al., "Cloning and expression of apical membrane water channel of rat kidney collecting tubule," *Nature* (11 Feb. 1993) 361:549–552.
Tonghui et al., "Cloning of a Novel Rat Kidney cDNA Homologous to CHIP28 and WCH–CD Water Channels" *Biochemical and Biophysical Research Communications* 197:654–659 (1993).
Zeidel et al., "Reconstitution of Functional Water Channels in Liposomes Containing Purified Red Cell CHIP 28 Protein" *Biochem.*31:7436–7440 (1992).
Nielson et al. "Cellular and subcellular immunolocalization of vasopressin–regulated water channel in rat kidney", *Proc. Nat. Acad. Sci. USA* 90:11663–11667 Dec. 1993.
Harris et al. "Current Understanding of the Cellular Biology and Molecular Structure of the Antidiuretic Hormone–stimulated Water Transport Pathway", *J. Clin. Invest.* 88:1–8 (1991).

Preston et al., "Appearance of Water Channels in Xenopus Oocytes Expressing Red Cell CHIP28 Protein", *Science* 256:385–387 (1992).
Denker et al., "Identification, Purification, and Partial Characterization of a Novel $M_r$ 28,000 Integral Membrane Protein from Erythrocytes and Renal Tubules", *J. Biol. Chem.* 263:15634–15642 (1988).
Preston et al., "Isolation of the cDNA for erythrocyte integral membrane protein of 28 kilodaltons: Member of an ancient channel family", *Proc. Natl. Acad. Sci. USA* 88:11110–11114 (1991).
Kornfeld et al., "Assembly of Asparagine–Linked Oligosaccharides", *Ann. Rev. Biochem.* 54:631–664 (1985).
Kennelly et al., "Consensus Sequences as Substrate Specificity Determinants for Protein Kinases and Protein Phosphatases", *J. Biol. Chem.* 266:15555–15558 (1991).
Pisano et al., "Genomic Cloning, Complete Nucleotide Sequence, and Structure of the Human Gene Encoding the Major Intrinsic Protein (MIP) of the Lens", *Genomics* 11:981–990 (1991).
Kent et al., "Nucleotide and derived amino–acid sequence of the major intrinsic protein of rateye–lens", *Nucl. Acid. Res.* 18:4256 (1990).
Pao et al., "Evolution of the MIP family of integral membrane transport proteins", *Mol. Microbiol.* 5:33–37 (1991).
Wistow et al., "Tandem sequence repeats in transmembrane channel proteins", *Trends Biochem. Sci.* 16:170–171 (1991).
Kyte et al., "A Simple Method for Displaying the Hydropathic Character of a Protein", *J. Mol. Biol.* 157:105–132 (1982).
Moriyama et al., "Detection of specific mRNAs in single nephron segments by use of the polymerase chain reaction", *Am. J. Physiol.* 258:F1470–F1474 (1990).
Terada et al., "RT–PCR microlocalization of mRNA for guanylyl cyclase–coupled ANF receptor in rat kidney", Am. J. Physiol. 261:F1080–F1087 (1991).
Handler, "Antidiuretic hormone moves membranes", *Am. J. Physiol.* 255:F375–F382 (1988).

(List continued on next page.)

*Primary Examiner*—Mindy Fleisher
*Assistant Examiner*—Bonnie D. Weiss
*Attorney, Agent, or Firm*—Morrison & Foerster LLP

[57] ABSTRACT

A WCH-1 cDNA probe specific to mRNA expressing a water channel localized in the kidney collecting tubule and complementary to said mRNA, and the sequence has been identified. The same is obtained by a) subjecting a single-chain cDNA prepared from kidney medullary mRNA of a mammal (rat) to PCR using, as degenerate primers, 5'-(T/C)T(T/C/A/G)AA(T/C)CC (T/C/A/G)GC(T/C/A/G)GT (T/C/A/G)AC-3' (SEQ ID NO:1) and 5'- AA(T/C/A/G)(G/C)(T/A)(T/C/A/G)C (G/T)(T/C/A/G)GC(T/C/A/G) GG(A/G)TT-3' (SEQ ID NO:2), and b) screening a kidney cDNA library of said mammal using a product of said PCR as a probe. WCH-1 protein molecules constituting said water channel can be produced by *Escherichia coli* producing protein molecules expressed by WCH-1 gene.

16 Claims, 9 Drawing Sheets

OTHER PUBLICATIONS

Zhang et al., "Water and urea permeability properties of Xenopus oocytes: expression of mRNA from toad urinary bladder", *Am. J. Physiol.* 260:C26–C34 (1991).

Sigel, "Use of Xenopus Oocytes for the Functional Expression of Plasma Membrane Proteins", *J. Membrane Biol.* 117:201–221 (1990).

Ganote et al., "Ultrastructural Studies of Vasopressin Effect on Isolated Perfused Renal Collecting Tubules of the Rabbit", *J. Cell Biol.* 36:355–367 (1968).

Kuwahara et al., "Rapid Development of Vasopressin–Induced Hydroosmosis in Kidney Collecting Tubules Measured by a New Fluorescence Technique", *Biophys. J.* 54:595–602 (1988).

Cohen et al., "Nonchromosomal Antibiotic Resistance in Bacteria: Genetic Transformation of *Eschericha coli* by R–Factor DNA", *Proc. Natl. Acad. Sci. USA* 69:2110–2114 (1972).

Bear et al., "Purification and Functional Reconstitution of the Cystic Fibrosis Transmembrane Conductance Regulator (CFTR)", *Cell* 68:809–818 (1992).

Kasahara et al., "Reconstitution and Purification of the D–Glucose Transporter from Human Erythrocytes", *J. Biol. Chem.*, 252:7384–7390 (1977).

Newman et al., "Solublization and Reconstitution of the Lactose Transport System from *Escherichia coli*", *J. Biol. Chem.*, 255:10583–10586 (1980).

Kagawa et al., "Partial Resolution of the Enzymes Catalyzing Oxidative Phosphorylation", *J. Biol. Chem.* 248:676–684 (1973).

Mishina et al., "Expression of functional acetylcholine receptor from cloned cDNAs", *Nature (London)* 307:604–608 (1984).

Dascal, "The Use of *Xenopus Oocytes* for the Study of Ion Channels", *CRC Crit. Rev. Biochem.* 22:317–387 (1987).

Orloff et al., *Am. J. Med.* 42:757–768 (1967).

Showsky et al., *J. Lab. Clin. Med.* 80:134–144 (1972).

Verkman, *Annu. Rev. Physiol.* 54:97–108 (1992).

Kozak, "An analysis of 5'–noncoding sequences from 699 vertebrate messenger RNAs", *Nucl. Acid Res.* 15:8125–8148 (1987).

Knepper et al., "Urinary Concentration and Dilution" Kidney (eds. Brenner, B. M. & Rector, F. C., Jr.) 445–482 W.B.Saunders, Philadelphia (1991).

Kirk et al., "Water Transport and Osmoregulation by Antidiuretic Hormone in Terminal Nephron Segments", Kidney: Physiologh and Pathophysiology (eds Seldin, D. W. and Giebisch, G.) 1693–1725 Raven Press, New York (1992).

```
                                              -84  AGAGAGAAGAGAAAGAGAGAG              -64
           GGAGGGAGGAAGAGCCACCCCCGTGGCCCAGACCCCTGGCCAGCGCGCAGAAGTCGGAGC               -4
           AGCATGTGGGAACTCAGATCCATAGCCTTCTCCCGAGCAGTGCTGGCTGAGTTCTTGGCC                57
WCH-1         M  W  E  L  R  S  I  A  F  S  R  A  V  L  A  E  F  L  A               19
CHIP28     M  A  S  E  F  K  K  K  L  F  W  R  A  V  V  A  E  F  L  A                20

ACGCTCCTTTTTGTCTTCTTTGGCCTTGGCTCAGCCCTC--------------------                96
WCH-1       T  L  L  F  V  F  F  G  L  G  S  A  L  -  -  -  -  -  -  -              32
CHIP28      T  T  L  F  V  F  I  S  I  G  S  A  L  G  F  K  Y  P  V  G              40

CAGTGGGCCAGCTCCCCACCCTCTGTGCTCCAGATCGCCGTGGCCTTTGGTCTGGGCATC                156
WCH-1       Q  W  A  S  S  P  P  S  V  L  Q  I  A  V  A  F  G  L  G  I              52
CHIP28      N  N  Q  T  A  V  Q  D  N  V  K  V  S  L  A  F  G  L  S  I              60

GGCATCCTGGTTCAGGCTCTGGGCCATGTCAGCGGGGCACACATCAACCCCGCCGTGACT                216
WCH-1       G  I  L  V  Q  A  L  G  H  V  S  G  A  H  I  N  P  A  V  T              72
CHIP28      A  T  L  A  Q  S  V  G  H  I  S  G  A  H  L  N  P  A  V  T              80

GTGGCATGCCTGGTGGGTTGCCATGTCTCCTTCCTTCGAGCTGCCTTCTATGTGGCTGCC                276
WCH-1       V  A  C  L  V  G  C  H  V  S  F  L  R  A  A  F  Y  V  A  A              92
CHIP28      L  G  L  L  L  S  C  Q  I  S  I  F  R  A  L  M  Y  I  I  A             100

CAGCTGCTGGGCGCCGTGGCTGGGGCTGCCATCCTCCATGAGATTACTCCAGTAGAAATC                336
WCH-1       Q  L  L  G  A  V  A  G  A  A  I  L  H  E  I  T  P  V  E  I             112
CHIP28      Q  C  V  G  A  I  V  A  T  A  I  L  S  G  I  T  S  S  L  T             120

CGTGGGGACCTGGCTGTCAATGCTCTCCACAACAACGCCACAGCTGGCCAGGCTGTGACT                396
WCH-1       R  G  D  L  A  V  N  A  L  H  N  N* A  T  A  G  Q  A  V  T             132
CHIP28      G  N  S  L  G  R  N  D  L  A  D  G  V  N  S  G  Q  G  L  G             140
```

FIG. IOA

```
              GTAGAGCTCTTCCTGACCATGCAGCTGGTGCTGTGCATCTTTGCCTCCACCGACGAGCGC   456
WCH-1    V  E  L  F  L  T  M  Q  L  V  L  C  I  F  A  S  T  D  E  R        152
CHIP28   I  E  I  I  G  T  L  Q  L  V  L  C  V  L  A  T  T  D  R  R        160

CGCGGTGACAACCTGGGTAGCCCTGCCCTCTCCATTGGTTTCTCTGTTACCCTGGGCCAC         516
WCH-1    R  G  D  N  L  G  S  P  A  L  S  I  G  F  S  V  T  L  G  H        172
CHIP28   R  R  D  L  G  G  S  A  P  L  A  I  G  L  S  V  A  L  G  H        180

CTCCTTGGGATCTATTTCACCGGTTGCTCCATGAATCCAGCCCGCTCCCTGGCTCCAGCA         576
WCH-1    L  L  G  I  Y  F  T  G  C  S  M  N  P  A  R  S  L  A  P  A        192
CHIP28   L  L  A  I  D  Y  T  G  C  G  I  N  P  A  R  S  F  G  S  A        200

GTTGTCACTGGCAAGTTTGATGATCACTGGGTCTTCTGGATCGGACCCCTGGTGGGCGCC         636
WCH-1    V  V  T  G  K  F  D  D  H  W  V  F  W  I  G  P  L  V  G  A        212
CHIP28   V  V  I  T  H  N  F  S  N  H  W  I  F  W  V  G  P  F  I  G  G     220

ATCATCGGCTCCCTCCTCTACAACTACCTGCTGTTCCCCTCGGCAAAGAGCCTGCAGGAG         696
WCH-1    I  I  G  S  L  L  Y  N  Y  L  L  F  P  S  A  K  S  L  Q  E        232
CHIP28   A  L  A  V  L  I  Y  D  F  I  L  A  P  R  S  S  D  L  T  D        240

CGCTTGGCAGTGCTCAAGGGCCTGGAGCCCGACACC---GACTGGGAGGAACGTGAAGTG         753
WCH-1    R  L  A  V  L  K  G  L  E  P  D  T  -  D  W  E  E  R  E  V        251
CHIP28   R  V  N  V  W  T  S  G  Q  V  E  E  Y  D  L  D  A  D  D  I        260

CGGCGGCGGCAGTCGGTGGAGCTCCACTCTCCTCAGAGCCTGCCTCGCGGCAGCAAGGCC         813
WCH-1    R  R  R  Q  S  V  E  L  H  S  P  Q  S  L  P  R  G  S  K  A        271
CHIP28   N  S  R  V  E  M  K  P  K                                         269

TGAGCTCCCCTGCAGCGCACCGCAGCTCAGCCGACCGACGGCTCGCCCCCTCCTTCCCCC         873
         TGACCCGTCGTCGGTTCCCAGTGCAGAGTAGCTGCTCCAGCGAGTGCAGTGAGCCTCAAG         933
         AAGGGGCTCGCCGGGAGCTGACAGTACCTCCGCCCGGAAGCCTTGAGCTACCCTCGAGCT         993
         CGCCCCTTGCAGGAACCAGACACTTGGGGACCGAGGCGTGGGGAGGGAAGGCAGGCCGGC        1053
         GAGAGACGGAGAGCTCTGGAGAGCCCGCTCTGGTGCCTGGGGAGAAGTGCATAGACTCCT        1113
         TCTGGGGGACTGTGCTTAGTGCATCTCATTTTATTAGGTTGTAAAAGTGCTCGTCTCCGC        1173
         GTATTTCTTTTCCTCACGAACAGAGTTTGCATGATCCTGAGCGTGATCCCGAGTGCCTGT        1233
         GGTGATACAGAGCCGGGGACTGTCATTCCCGCTTTGGCCTTCTTCTCCTGTACCTGCAAT        1293
         AAATCCACTATCTCTGAAAAAAAAAAAAAAA                                    1324
```

FIG. 10B

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i x ) FEATURE:
        ( A ) NAME/KEY: misc_difference
        ( B ) LOCATION: replace(1, "")
        ( D ) OTHER INFORMATION: /note= "This position is (T/C)."

( i x ) FEATURE:
        ( A ) NAME/KEY: misc_difference
        ( B ) LOCATION: replace(3, "")
        ( D ) OTHER INFORMATION: /note= "This position is
        ( T / C / A / G )."

( i x ) FEATURE:
        ( A ) NAME/KEY: misc_difference
        ( B ) LOCATION: replace(6, "")
        ( D ) OTHER INFORMATION: /note= "This position is (T/C)."

( i x ) FEATURE:
        ( A ) NAME/KEY: misc_difference
        ( B ) LOCATION: replace(9, "")
        ( D ) OTHER INFORMATION: /note= "This position is
        ( T / C / A / G )."

( i x ) FEATURE:
        ( A ) NAME/KEY: misc_difference
        ( B ) LOCATION: replace(12, "")
        ( D ) OTHER INFORMATION: /note= "This position is
        ( T / C / A / G )."

( i x ) FEATURE:
        ( A ) NAME/KEY: misc_difference
        ( B ) LOCATION: replace(15, "")
        ( D ) OTHER INFORMATION: /note= "This position is
        ( T / C / A / G )."

( x i ) SEQUENCE DESCRIPTION: SEQ ID NO:1:

N T N A A N C C N G C N G T N A C        1 7

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(3, "")
        ( D ) OTHER INFORMATION: /note= "This position is
        ( T / C / A / G )."

( i x ) FEATURE:
        ( A ) NAME/KEY: misc_difference
        ( B ) LOCATION: replace(4, "")
        ( D ) OTHER INFORMATION: /note= "This position is (G/C)."

( i x ) FEATURE:
        ( A ) NAME/KEY: misc_difference
        ( B ) LOCATION: replace(5, "")
        ( D ) OTHER INFORMATION: /note= "This position is (T/A)."

( i x ) FEATURE:
        ( A ) NAME/KEY: misc_difference
        ( B ) LOCATION: replace(6, "")
        ( D ) OTHER INFORMATION: /note= "This position is
        ( T / C / A / G )."

( i x ) FEATURE:
        ( A ) NAME/KEY: misc_difference
        ( B ) LOCATION: replace(8, "")
        ( D ) OTHER INFORMATION: /note= "This position is (G/T)."

( i x ) FEATURE:
        ( A ) NAME/KEY: misc_difference
        ( B ) LOCATION: replace(9, "")
        ( D ) OTHER INFORMATION: /note= "This position is
        ( T / C / A / G )."

-continued (ix) FEATURE:
  (A) NAME/KEY: misc_difference
  (B) LOCATION: replace(12, "")
  (D) OTHER INFORMATION: /note= "This position is (T/C/A/G)."

(ix) FEATURE:
  (A) NAME/KEY: misc_difference
  (B) LOCATION: replace(15, "")
  (D) OTHER INFORMATION: /note= "This position is (A/G)."

(xi) SEQUENCE DESCRIPTION: SEQ ID NO:2:

AANNNNCNNG CNGGNTT       17

(2) INFORMATION FOR SEQ ID NO:3:

(i) SEQUENCE CHARACTERISTICS:
    (A) LENGTH: 1408 base pairs
    (B) TYPE: nucleic acid
    (C) STRANDEDNESS: single
    (D) TOPOLOGY: linear (ix) FEATURE:
    (A) NAME/KEY: CDS
    (B) LOCATION: 85..897

(xi) SEQUENCE DESCRIPTION: SEQ ID NO:3:

| | | | | |
|---|---|---|---|---|
| AGAGAGAAGA GAAAGAGAGA GGGAGGGAGG AAGAGCCACC CCCGTGGCCC AGACCCCTGG | | | | 60 |

```
CCAGCGCGCA GAAGTCGGAG CAGC ATG TGG GAA CTC AGA TCC ATA GCC TTC         111
                          Met Trp Glu Leu Arg Ser Ile Ala Phe
                           1               5

TCC CGA GCA GTG CTG GCT GAG TTC TTG GCC ACG CTC CTT TTT GTC TTC         159
Ser Arg Ala Val Leu Ala Glu Phe Leu Ala Thr Leu Leu Phe Val Phe
 10              15                  20                  25

TTT GGC CTT GGC TCA GCC CTC CAG TGG GCC AGC TCC CCA CCC TCT GTG         207
Phe Gly Leu Gly Ser Ala Leu Gln Trp Ala Ser Ser Pro Pro Ser Val
             30                  35                  40

CTC CAG ATC GCC GTG GCC TTT GGT CTG GGC ATC GGC ATC CTG GTT CAG         255
Leu Gln Ile Ala Val Ala Phe Gly Leu Gly Ile Gly Ile Leu Val Gln
         45                  50                  55

GCT CTG GGC CAT GTC AGC GGG GCA CAC ATC AAC CCC GCC GTG ACT GTG         303
Ala Leu Gly His Val Ser Gly Ala His Ile Asn Pro Ala Val Thr Val
     60                  65                  70

GCA TGC CTG GTG GGT TGC CAT GTC TCC TTC CTT CGA GCT GCC TTC TAT         351
Ala Cys Leu Val Gly Cys His Val Ser Phe Leu Arg Ala Ala Phe Tyr
 75                  80                  85

GTG GCT GCC CAG CTG CTG GGC GCC GTG GCT GGG GCT GCC ATC CTC CAT         399
Val Ala Ala Gln Leu Leu Gly Ala Val Ala Gly Ala Ala Ile Leu His
 90              95                 100                 105

GAG ATT ACT CCA GTA GAA ATC CGT GGG GAC CTG GCT GTC AAT GCT CTC         447
Glu Ile Thr Pro Val Glu Ile Arg Gly Asp Leu Ala Val Asn Ala Leu
             110                 115                 120

CAC AAC AAC GCC ACA GCT GGC CAG GCT GTG ACT GTA GAG CTC TTC CTG         495
His Asn Asn Ala Thr Ala Gly Gln Ala Val Thr Val Glu Leu Phe Leu
         125                 130                 135

ACC ATG CAG CTG GTG CTG TGC ATC TTT GCC TCC ACC GAC GAG CGC CGC         543
Thr Met Gln Leu Val Leu Cys Ile Phe Ala Ser Thr Asp Glu Arg Arg
     140                 145                 150

GGT GAC AAC CTG GGT AGC CCT GCC CTC TCC ATT GGT TTC TCT GTT ACC         591
Gly Asp Asn Leu Gly Ser Pro Ala Leu Ser Ile Gly Phe Ser Val Thr
 155                 160                 165

CTG GGC CAC CTC CTT GGG ATC TAT TTC ACC GGT TGC TCC ATG AAT CCA         639
Leu Gly His Leu Leu Gly Ile Tyr Phe Thr Gly Cys Ser Met Asn Pro
 170                 175                 180                 185
```

| | | | | | | | | | | | | | | | | |
|---|---|---|---|---|---|---|---|---|---|---|---|---|---|---|---|---|
| GCC | CGC | TCC | CTG | GCT | CCA | GCA | GTT | GTC | ACT | GGC | AAG | TTT | GAT | GAT | CAC | 687 |
| Ala | Arg | Ser | Leu | Ala | Pro | Ala | Val | Val | Thr | Gly | Lys | Phe | Asp | Asp | His | |
| | | | | 190 | | | | | 195 | | | | | 200 | | |
| TGG | GTC | TTC | TGG | ATC | GGA | CCC | CTG | GTG | GGC | GCC | ATC | ATC | GGC | TCC | CTC | 735 |
| Trp | Val | Phe | Trp | Ile | Gly | Pro | Leu | Val | Gly | Ala | Ile | Ile | Gly | Ser | Leu | |
| | | | 205 | | | | 210 | | | | | | 215 | | | |
| CTC | TAC | AAC | TAC | CTG | CTG | TTC | CCC | TCG | GCA | AAG | AGC | CTG | CAG | GAG | CGC | 783 |
| Leu | Tyr | Asn | Tyr | Leu | Leu | Phe | Pro | Ser | Ala | Lys | Ser | Leu | Gln | Glu | Arg | |
| | | 220 | | | | | 225 | | | | | 230 | | | | |
| TTG | GCA | GTG | CTC | AAG | GGC | CTG | GAG | CCC | GAC | ACC | GAC | TGG | GAG | GAA | CGT | 831 |
| Leu | Ala | Val | Leu | Lys | Gly | Leu | Glu | Pro | Asp | Thr | Asp | Trp | Glu | Glu | Arg | |
| | 235 | | | | 240 | | | | | 245 | | | | | | |
| GAA | GTG | CGG | CGG | CGG | CAG | TCG | GTG | GAG | CTC | CAC | TCT | CCT | CAG | AGC | CTG | 879 |
| Glu | Val | Arg | Arg | Arg | Gln | Ser | Val | Glu | Leu | His | Ser | Pro | Gln | Ser | Leu | |
| 250 | | | | | 255 | | | | | 260 | | | | | 265 | |
| CCT | CGC | GGC | AGC | AAG | GCC | TGAGCTCCCC | | TGCAGCGCAC | | CGCAGCTCAG | | | | | | 927 |
| Pro | Arg | Gly | Ser | Lys | Ala | | | | | | | | | | | |
| | | | | 270 | | | | | | | | | | | | |

| | | | | |
|---|---|---|---|---|
| CCGACCGACG | GCTCGCCCCC | TCCTTCCCCC | TGACCCGTCG | TCGGTTCCCA | GTGCAGAGTA | 987 |
| GCTGCTCCAG | CGAGTGCAGT | GAGCCTCAAG | AAGGGGCTCG | CCGGGAGCTG | ACAGTACCTC | 1047 |
| CGCCCGGAAG | CCTTGAGCTA | CCCTCGAGCT | CGCCCCTTGC | AGGAACCAGA | CACTTGGGGA | 1107 |
| CCGAGGCGTG | GGGAGGGAAG | GCAGGCCGGC | GAGAGACGGA | GAGCTCTGGA | GAGCCCGCTC | 1167 |
| TGGTGCCTGG | GGAGAAGTGC | ATAGACTCCT | TCTGGGGGAC | TGTGCTTAGT | GCATCTCATT | 1227 |
| TTATTAGGTT | GTAAAAGTGC | TCGTCTCCGC | GTATTTCTTT | TCCTCACGAA | CAGAGTTTGC | 1287 |
| ATGATCCTGA | GCGTGATCCC | GAGTGCCTGT | GGTGATACAG | AGCCGGGGAC | TGTCATTCCC | 1347 |
| GCTTTGGCCT | TCTTCTCCTG | TACCTGCAAT | AAATCCACTA | TCTCTGAAAA | AAAAAAAAAA | 1407 |
| A | | | | | | 1408 |

( 2 ) INFORMATION FOR SEQ ID NO:4:

( i ) SEQUENCE CHARACTERISTICS:
    ( A ) LENGTH: 271 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Trp | Glu | Leu | Arg | Ser | Ile | Ala | Phe | Ser | Arg | Ala | Val | Leu | Ala | Glu |
| 1 | | | | 5 | | | | | 10 | | | | | 15 | |
| Phe | Leu | Ala | Thr | Leu | Leu | Phe | Val | Phe | Phe | Gly | Leu | Gly | Ser | Ala | Leu |
| | | | 20 | | | | 25 | | | | | 30 | | | |
| Gln | Trp | Ala | Ser | Ser | Pro | Pro | Ser | Val | Leu | Gln | Ile | Ala | Val | Ala | Phe |
| | | | 35 | | | | 40 | | | | | 45 | | | |
| Gly | Leu | Gly | Ile | Gly | Ile | Leu | Val | Gln | Ala | Leu | Gly | His | Val | Ser | Gly |
| | | 50 | | | | 55 | | | | | 60 | | | | |
| Ala | His | Ile | Asn | Pro | Ala | Val | Thr | Val | Ala | Cys | Leu | Val | Gly | Cys | His |
| 65 | | | | | 70 | | | | 75 | | | | | 80 | |
| Val | Ser | Phe | Leu | Arg | Ala | Ala | Phe | Tyr | Val | Ala | Ala | Gln | Leu | Leu | Gly |
| | | | | 85 | | | | | 90 | | | | | 95 | |
| Ala | Val | Ala | Gly | Ala | Ala | Ile | Leu | His | Glu | Ile | Thr | Pro | Val | Glu | Ile |
| | | | 100 | | | | | 105 | | | | | 110 | | |
| Arg | Gly | Asp | Leu | Ala | Val | Asn | Ala | Leu | His | Asn | Asn | Ala | Thr | Ala | Gly |
| | | | 115 | | | | | 120 | | | | | 125 | | |
| Gln | Ala | Val | Thr | Val | Glu | Leu | Phe | Leu | Thr | Met | Gln | Leu | Val | Leu | Cys |
| | | | 130 | | | | | 135 | | | | | 140 | | |

| | | | | | | | | | | | | | | |
|---|---|---|---|---|---|---|---|---|---|---|---|---|---|---|
| Ile<br>145 | Phe | Ala | Ser | Thr | Asp<br>150 | Glu | Arg | Arg | Gly | Asp<br>155 | Asn | Leu | Gly | Ser | Pro<br>160 |
| Ala | Leu | Ser | Ile | Gly<br>165 | Phe | Ser | Val | Thr | Leu<br>170 | Gly | His | Leu | Leu | Gly<br>175 | Ile |
| Tyr | Phe | Thr | Gly<br>180 | Cys | Ser | Met | Asn | Pro<br>185 | Ala | Arg | Ser | Leu | Ala<br>190 | Pro | Ala |
| Val | Val | Thr<br>195 | Gly | Lys | Phe | Asp | Asp<br>200 | His | Trp | Val | Phe | Trp<br>205 | Ile | Gly | Pro |
| Leu | Val<br>210 | Gly | Ala | Ile | Ile | Gly<br>215 | Ser | Leu | Leu | Tyr | Asn<br>220 | Tyr | Leu | Leu | Phe |
| Pro<br>225 | Ser | Ala | Lys | Ser | Leu<br>230 | Gln | Glu | Arg | Leu | Ala<br>235 | Val | Leu | Lys | Gly | Leu<br>240 |
| Glu | Pro | Asp | Thr | Asp<br>245 | Trp | Glu | Glu | Arg | Glu<br>250 | Val | Arg | Arg | Arg | Gln<br>255 | Ser |
| Val | Glu | Leu | His<br>260 | Ser | Pro | Gln | Ser | Leu<br>265 | Pro | Arg | Gly | Ser | Lys<br>270 | Ala | |

( 2 ) INFORMATION FOR SEQ ID NO:5:

( i ) SEQUENCE CHARACTERISTICS:
        ( A ) LENGTH: 269 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

| | | | | | | | | | | | | | | |
|---|---|---|---|---|---|---|---|---|---|---|---|---|---|---|
| Met<br>1 | Ala | Ser | Glu | Phe<br>5 | Lys | Lys | Lys | Leu | Phe<br>10 | Trp | Arg | Ala | Val | Val<br>15 | Ala |
| Glu | Phe | Leu | Ala<br>20 | Thr | Thr | Leu | Phe | Val<br>25 | Phe | Ile | Ser | Ile | Gly<br>30 | Ser | Ala |
| Leu | Gly | Phe<br>35 | Lys | Tyr | Pro | Val | Gly<br>40 | Asn | Asn | Gln | Thr | Ala<br>45 | Val | Gln | Asp |
| Asn | Val<br>50 | Lys | Val | Ser | Leu | Ala<br>55 | Phe | Gly | Leu | Ser | Ile<br>60 | Ala | Thr | Leu | Ala |
| Gln<br>65 | Ser | Val | Gly | His | Ile<br>70 | Ser | Gly | Ala | His | Leu<br>75 | Asn | Pro | Ala | Val | Thr<br>80 |
| Leu | Gly | Leu | Leu | Leu<br>85 | Ser | Cys | Gln | Ile | Ser<br>90 | Ile | Phe | Arg | Ala | Leu<br>95 | Met |
| Tyr | Ile | Ile | Ala<br>100 | Gln | Cys | Val | Gly | Ala<br>105 | Ile | Val | Ala | Thr | Ala<br>110 | Ile | Leu |
| Ser | Gly | Ile<br>115 | Thr | Ser | Ser | Leu | Thr<br>120 | Gly | Asn | Ser | Leu | Gly<br>125 | Arg | Asn | Asp |
| Leu | Ala<br>130 | Asp | Gly | Val | Asn | Ser<br>135 | Gly | Gln | Gly | Leu | Gly<br>140 | Ile | Glu | Ile | Ile |
| Gly<br>145 | Thr | Leu | Gln | Leu | Val<br>150 | Leu | Cys | Val | Leu | Ala<br>155 | Thr | Thr | Asp | Arg | Arg<br>160 |
| Arg | Arg | Asp | Leu | Gly<br>165 | Gly | Ser | Ala | Pro | Leu<br>170 | Ala | Ile | Gly | Leu | Ser<br>175 | Val |
| Ala | Leu | Gly | His<br>180 | Leu | Leu | Ala | Ile | Asp<br>185 | Tyr | Thr | Gly | Cys | Gly<br>190 | Ile | Asn |
| Pro | Ala | Arg<br>195 | Ser | Phe | Gly | Ser | Ala<br>200 | Val | Ile | Thr | His | Asn<br>205 | Phe | Ser | Asn |
| His | Trp<br>210 | Ile | Phe | Trp | Val | Gly<br>215 | Pro | Phe | Ile | Gly | Gly<br>220 | Ala | Leu | Ala | Val |
| Leu<br>225 | Ile | Tyr | Asp | Phe | Ile<br>230 | Leu | Ala | Pro | Arg | Ser<br>235 | Ser | Asp | Leu | Thr | Asp<br>240 |

-continued

```
    Arg  Val  Asn  Val  Trp  Thr  Ser  Gly  Gln  Val  Glu  Glu  Tyr  Asp  Leu  Asp
                        245                     250                     255

Ala  Asp  Asp  Ile  Asn  Ser  Arg  Val  Glu  Met  Lys  Pro  Lys
                        260                     265
```

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:6:

TGGGATCTAT TTCACCGG 18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:7:

ACAGGCACTC GGGATCAC 18

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:8:

```
    Val  Glu  Leu  His  Ser  Pro  Gln  Ser  Leu  Pro  Arg  Gly  Ser  Lys  Ala
     1              5                        10                       15
```

WATER CHANNEL

This application is a continuation of application Ser. No. 08/126,365, filed 24 Sep. 1993, now abandoned.

FIELD OF THE INVENTION

This invention relates to a gene and protein molecules forming a vasopressin-regulated water channel WCH-1 localized in the kidney collecting tubule.

Using the gene and the protein molecules, a screening method for water diuretics may be established, while a high water-permeable artificial membrane and liposome into which the WCH-1 protein has been incorporated may be produced.

RELATED ART

Urine concentration is mandatory for most mammals in order to prevent loss of body water. Concentrated urine is produced, in response to vasopressin, by the transepithelial water recovery from the lumen of the kidney collecting tubule through high water permeable membranes (Orloff, J. & Handler, J. S. Am. J. Med. 42, 757–768 (1967); Knepper, M. A. & Rector, F. C. Jr. in The Kidney (eds Brenner, B. M. & Rector, F. C. Jr.) 445–482 (W. B. Saunders, Philadelphia, (1991))). In this nephron segment, vasopressin regulates water permeability by endo- and exocytosis of water channels from and to the apical membrane (Handler, J. S. Am. J. Physiol. 255, F375–F382 (1988); Harris, H. W. Jr., Strange, K. & Zeidel, M. L. J. Clin. Invest. 88, 1–8 (1991)).

Recently, it has been shown that CHIP 28 is a water channel in red blood cell membranes (RBC) and in kidney proximal tubule (Preston, G. M., Carrol, T. P., Guggino, W. B. & Agre, P. Science 256, 385–387 (1992)). However, CHIP 28 is not expressed in the collecting tubule (Denker, B. M., Smith, B. L., Kuhajda, F. P. & Agre, P. J. Biol. Chem. 263, 15634–15642 (1988)).

SUMMARY OF THE DISCLOSURE

Problem to be Solved by the Invention

The presence of the water channel in the kidney collecting tubule has not been proved to date. If the presence of the water channel is demonstrated, isolated and identified, the basis for clarification of the basic principle of the kidney may be achieved, while the basis for therapy of a variety of kidney diseases may be found.

It is therefore an object of the present invention to obtain a water channel of the kidney collecting tubule in an isolated form and to obtain its clone or reproduction and means for cloning or producing the same.

It is a further object of the present invention to provide an artificial membrane in which the water channel of the present invention is incorporated.
Definition In the present invention, WCH-1 means a vasopressin-regulated water channel localized in the kidney collecting tubule, while the gene capable of expressing such water channel is termed WCH-1 gene.
Inventive Solution for the Problem According to the present invention, the above objects may be achieved by isolation of a WCH-1 cDNA probe, *Escherichia coli* producing WCH-1 protein molecules, WCH-1 protein molecules produced by the *Escherichia coli*, and a method for producing the WCH-1 protein molecules. Besides, the lipid membrane in which the WCH-1 protein is incorporated is produced.

Concretely the present invention is summarized as follows:

A WCH-1 cDNA probe which is specific to mRNA expressing the water channel localized in the kidney collecting tubule and which is complementary to said mRNA.

A WCH-1 cDNA probe which is specific to mRNA expressing the vasopressin-regulated water channel and which is complementary to said mRNA.

Clone of the WCH-1 cDNA obtained by a) subjecting a single-chain cDNA prepared from kidney medullary mRNA of a mammal to PCR using, as degenerate primers, 5'-(T/C)T(T/C/A/G)AA(T/C)CC (T/C/A/G)GC(T/C/A/G)GT (T/C/A/G)AC-3' (SEQ ID NO:1) and 5'-AA(T/G/A/G)(G/C)(T/A)(T/C/A/G)C(G/T)(T/C/A/G)GC(T/G/A/G) GG(A/G)TT-3' (SEQ ID NO:2), and b) screening a kidney cDNA library of said mammal using a product of said PCR as a probe. The kidney is preferably furnished by a rat.

A base sequence of WCH-1 cDNA represented by sequence number 1 in the Table of Sequence Description below [SEQ ID NO:5].

A WCH-1 mRNA probe obtained by employing the WCH-1 cDNA probe as a template.

A WCH-1 protein molecule constituting a water channel localized in the kidney collecting tubule, or a WCH-1 protein molecule constituting a vasopressin-regulated water channel.

An amino acid sequence representing the above-mentioned WCH-1 protein molecule coded by the base sequence shown by sequence number 1 in the Table of Sequence Description below [SEQ ID NO:5].

A recombinant plasmid in which a WCH-1 gene represented by the base sequence shown by the sequence number 1 is incorporated in an expressing vector.

A recombinant plasmid in which said expressing vector is preferably pSPORT and said WCH-1 gene is inserted into sectioned sites of said pSPORT with Not-I and Sal-I.

*Escherichia coli* producing WCH-1 protein molecules, expressed by the WCH-1 gene, constituting a water channel localized in the kidney collecting tubule, or *Escherichia coli* producing WCH-1 protein molecule, expressed by the WCH-1 gene, constituting a vasopressin-regulated water channel (The *Escherichia coli* have been deposited at the Microorganism Laboratory of the Agency of Industrial Science and Technology under designation for identification of "*Escherichia coli* rWCH-1" under deposition number of FERM P-13171).

The WCH-1 protein molecule produced by said *Escherichia coli*.

A method for producing the WCH-1 protein molecule wherein the WCH-1 protein molecule is obtained using said *Escherichia coli*.

Preferably, said *Escherichia coil* is: one obtained by introducing the recombinant plasmid which has been obtained by inserting the WCH-1 gene into the expressing vector pSPORT into *Escherichia coli* DH10α for transformation, and more preferably said *Escherichia coli* being one contains the plasmid in which said WCH-1 gene is introduced into sectioned sites of pSPORT by Not-I and Sal-I, or said *Escherichia coli* being one having the plasmid produced employing the vector (pSPORT) the expression of which may be derived by addition of isopropyl β-D-thiogalactoside (IPTG), host (DH10α) family.

A lipid membrane containing the WCH-1 protein molecule.

Liposome formed of a lipid membrane containing the WCH-1 protein molecules.

Effect of the Invention

The following meritorious effects may be expected from the present invention.

1) The presence of the water channel in the kidney collecting tubule is clearly demonstrated, isolated and identifide, the basis for clarification of the basic principle of the kidney has now been established.

2) Since the basic principle of the kidney will be clarified, a new guideline is provided in giving a diagnosis of kidney lesions.

3) Also, since the basic principle of the kidney is clarified, a new guideline is provided in therapy for kidney lesions or a material for therapy of kidney lesions.

4) The WCH-1 water channel may be expressed on the living membrane by introducing WCH-1 cDNA or mRNA into cells.

5) High water-permeable WCH-1 protein may be acquired easily in large quantities by the gene-operated *Escherichia coli* according to the present invention.

6) A screening method for water diuretics may be established.

7) A high water-permeable artificial membrane in which is incorporated the WCH-1 protein may be produced.

8) High water-permeable artificial liposome in which is incorporated the WCH-1 protein may be produced.

Introduction of the Description

The following description is made by reference to the cloning of cDNA for WCH-1 which is a new water channel of the apical membrane of the kidney collecting tubule. WCH-1 is identical up to 42% in amino acid sequence to CHIP 28. WCH-1 transcripts are detected only in the kidney collecting tubule. Immunohistochemically, WCH-1 is localized to the apical region of the kidney collecting tubule cells. Expression of WCH-1 in Xenopus oocytes markedly increased osmotic water permeability. Interestingly, dehydration markedly stimulates WCH-1 mRNA in rat kidney, without stimulating CHIP 28 mRNA. The functional expression by WCH-1 and the limited localization of WCH-1 to the apical region of the kidney collecting tubule suggest that WCH-1 is the vasopressin-regulated water channel.

Figure 4:
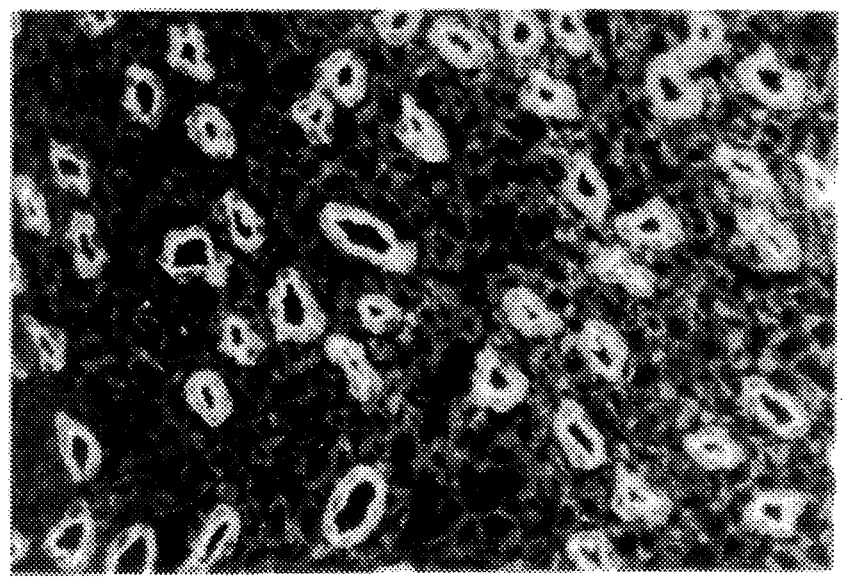
Figure 5:

The expressions and abbreviations in English are as follows:

PCT; bent part of a proximal tubule,
TDL; thin descending leg of the loop of Henle,
TAL; thin ascending leg of a medulla,
MAL; thick ascending leg of a medulla,
CCD; cortex collective duct,
OMCD; outer medulla collective duct,
IMCD; inner medulla collective duct,
RT(−); reaction without reverse transriptase, FIG. 4 is a microscopic photo, with a magnification factor of 100, showing the chromosomal tissue of a rat's kidney medulla portion by the fluorescent antibody technique employing anti-WCH1/C, FIG. 5 is a microscopic photo, with a magnification factor of 100, showing a chromosomal tissue by the fluorescent antibody technique employing anti-WCH1/C previously pre-incubated with a corresponding peptide antigen.

Figure 6:
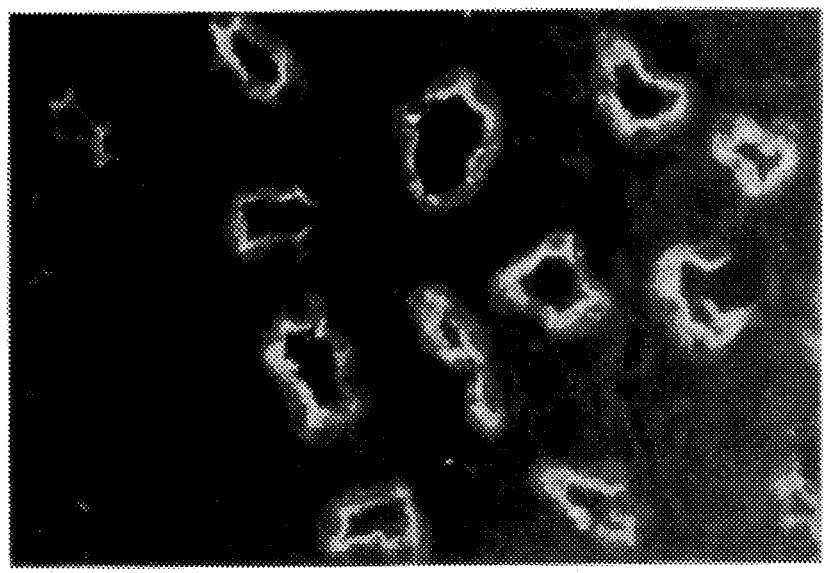

FIG. 6 is a microscopic photo, with a magnification factor of 400, showing a chromosomal tissue of a rat's kidney medulla by the fluorescent antibody technique employing anti-WCH1/C.

Figure 7:
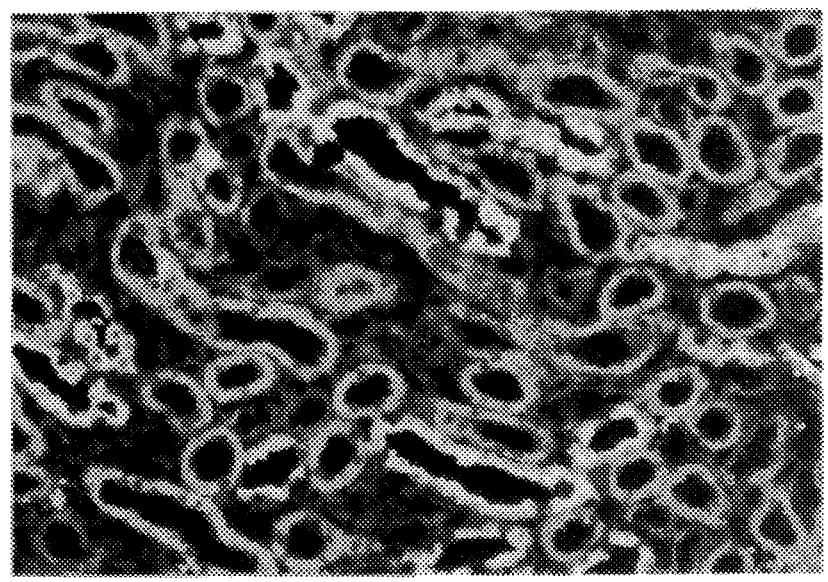

FIG. 7 is a microscopic photo, with a magnification factor of 100, showing a chromosomal tissue of a rat's kidney cortex portion by the fluorescent antibody technique employing anti-WCH1/C.

Figure 8A:
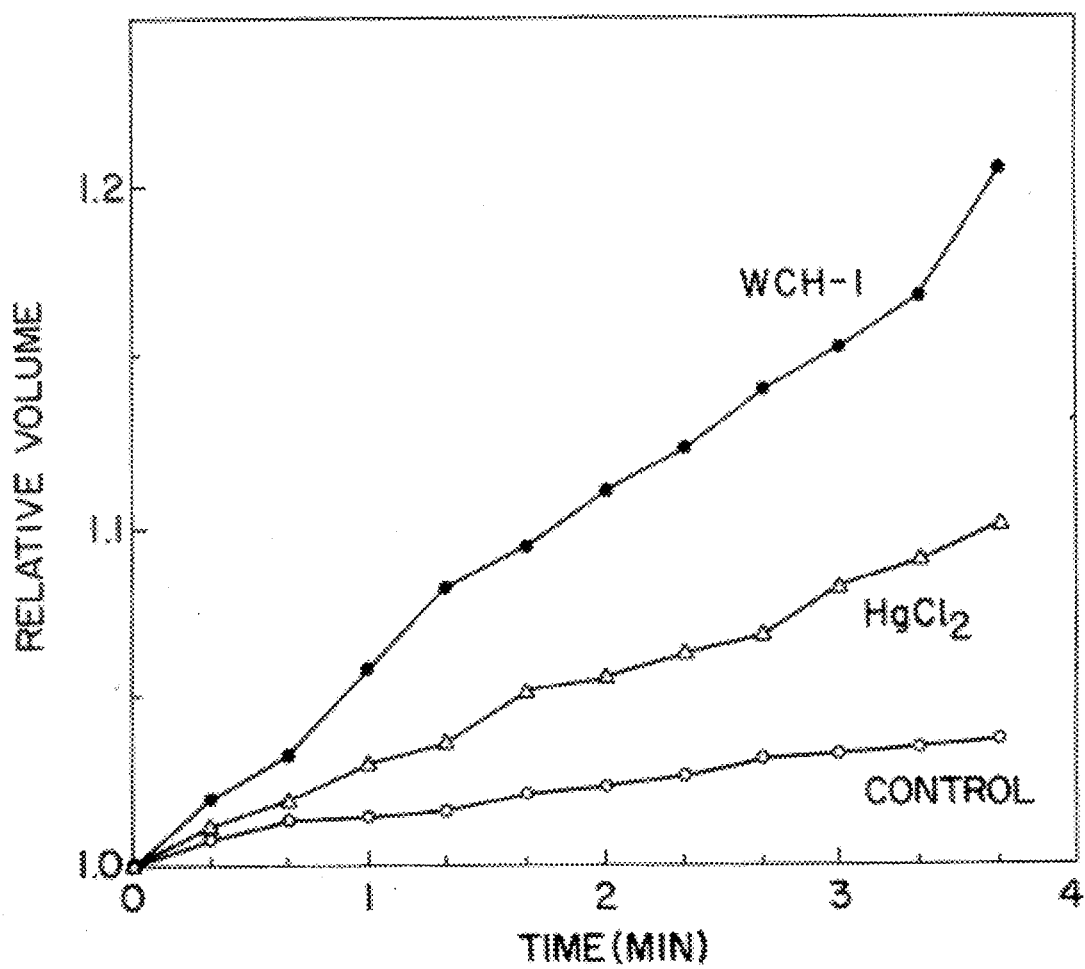

FIG. 8(a) is a graph showing a time-dependent volumetric increase of the oocytes injected with 20 ng of WCH-1RNA (WCH-1) and with water (for comparison or control).

Figure 8B:
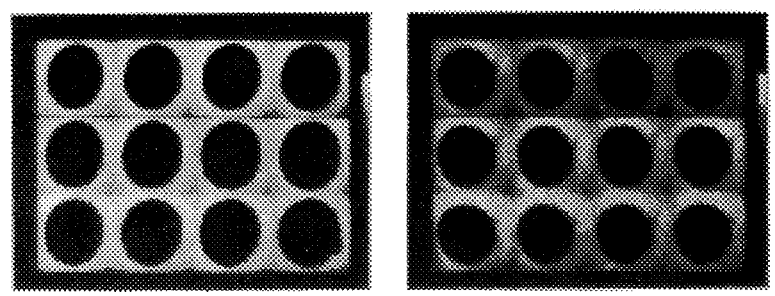

FIG. 8(b) is a microscopic photo of the oocyte injected with WCH-1 RNA or with water.

Figure 9:
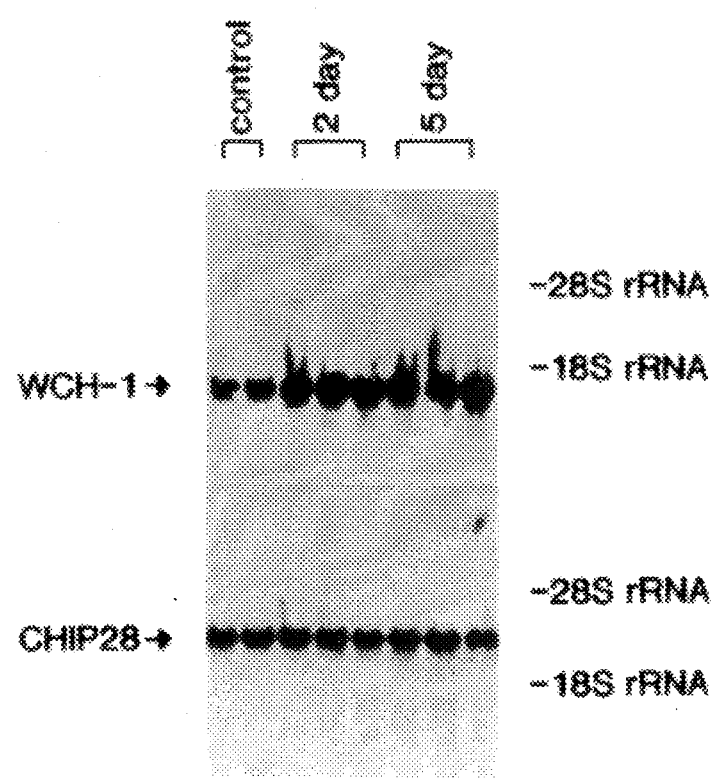

FIG. 9 is a photo showing results of the Northern blot analysis showing changes in the amount of WCH-1 and CHIP-28 mRNA in the rat's kidney following prolonged dehydration.

FIG. 10 (SEQ ID NO:3, SEQ ID NO:4, and SEQ ID NO:5) is a sequence diagram showing the coincidence of the WCH-1 cDNA nucleotide sequence and its presumed amino acid sequence with human CHIP 28.

The abbreviations of the amino acid sequences are as follows:

A; alanine (Ala),
C; cysteine (Cys),
D; aspartic acid (Asp),
E; glutamic acid (Glu),
F; phenylalanine (Phe),
G; glycine (Gly),
H; histidine (His),
I; isoleucine (Ile),
K; lysine (Lys),
L; leucine (Leu),
M; methionine (Met),
N; asparagine (Asn),
P; proline (pro),
Q; glutamine (Glu),
R; arginine (Arg),
S; serine (Ser),
T; threonine (Thr),
V; valine (Val),
W; tryptophane (Trp),
Y; tyrosine (Tyr),

DESCRIPTION OF THE PREFERRED EMBODIMENTS

Isolation and Determination of Base Sequence of WCH-1 mRNA

Rat kidney medulla poly(A)$^+$RNA was submitted to reverse transcription and 30 cycles of PCR with 6 µM each of two degenerate primers, 5'-(T/C)T(T/C/A/G)AA(T/C)CC(T/C/A/G)GC(T/C/A/G)GT(T/C/A/G)AC-3' (SEQ ID NO:1) and 5'-AA(T/C/A/G)(G/C)(T/A)(T/C/A/G)C(G/T)

(T/C/A/G)GC(T/C/A/G) GG(A/G)TT-3' (SEQ ID NO:2), synthesized based on conserved amino acid sequences of the MIP family (Leu-Asn-Pro-Ala-Val-Thr, Asn-Pro-Ala-Arg-Ser-Phe, respectively) (Wistow, G. J. Pisano, M. M. & Chepelinsky A. B. Trends Biochem. Sci. 16, 170–171 (1991)). The cycle consisted in denaturation at 94° C. for 1 minute, annealing at 50 ° C. for one minute and extension at 72° C. for three minutes, followed by a final extension for 7 minutes.

A band of ~370 bp PCR products was isolated by gel electrophoresis and subcloned into the plasmid vector PCR 1000 (Invitrogen). 24 clones were sequenced using the fluorescence DNA sequencer 373A (Applied Biosystems) with –21M13 and M13R fluorescent primers.

A clone (pMWC41) was obtained with a 369 bp insert of 58% nucleotide sequence identity and 45% deduced amino acid sequence identity to human CHIP 28.

Another clone (prCHIP 28) was a 369 bp insert of 88% nucleotide sequence identity and 95% deduced amino acid sequence identity to human CHIP 28.

The clone pMWC41 was used to screen a $2 \times 10^7$ recombinant rat kidney cDNA library constructed in the Not-I/Sal-I site of the λgt 22 vector (BRL). Under stringent condition (hybridization at 6×SSPE, 50% formamide, 42° C.; washing at 2×SSC, 0.5% SDS, 42° C.), a positive clone (WCH-1) was isolated with ~1.4 kb insert.

The cDNA insert was subcloned into the Not-I/Sal-I site of the pSPORT vector (BRL) and the base sequence as well as the amino acid sequence was determined by the Sanger dideoxynucleotide chain termination method using Sequenase (USB).

FIG. 10 shows the sequence for WCH-1. FIG. 10 shows nucleotide sequence for the WCH-1 cDNA and alignment of its deduced amino acid sequence with that of human CHIP 28 (Preston, G. M. & Agre, P. Proc. Natl. Acad. Sci. USA. 88, 11110–11114 (1991)). Conserved residues are shown in boxes and deduced transmembrane domains (Kyte, J. & Doolittle, R. F. J. Mol. Biol. 157, 105–132 (1982)) are underlined.

* indicates consensus sequences for potential N-linked glycosylation sites (Kornfeld, R. & Kornfeld, S. Ann. Rev. Biochem. 54, 631–664 (1985)), ▽, ♦ and ● indicate phosphorylation sites for cAMP-dependent protein kinase, for protein kinase C and for casein kinase II, respectively. The poly(A)$^+$ track at the end of the cDNA begins 14nt after the AATAAA cleavage and polyadenylation sequence.

The first ATG was determined as an initiation codon on the basis of the Kozak's consensus A at position –3 (Kozak, M. Nucl. Acid Res. 15, 8127–8146 (1987)) and the sequence identity of the first seven amino acids to human MIP (Pisano, M. M. & Chepelinsky, A. B. Genomics 11, 981–990 (1991)).

The longest open reading frame encodes a 271-amino acid protein (Mr 28928) with 42.7% sequence identity with human CHIP 28 and 59.1% sequence identity with rat MIP (Kent N. A. Shiels, A. Nucl. Acid. Res. 18, 4256 (1990)). Conserved residues in WCH-1 and the members of the MIP family (Pao, G. M. et al., Mol. Microbiol. 5, 33–37 (1991)) and internal tandem repeats (Wistow, G. J., Pisano, M. M. & Chepelinsky, A. B. Trends Biochem. Sci. 16, 170–171 (1991)) in the WCH-1 sequence suggest that the WCH-1 is a new member of the MIP family.

Figure 1:
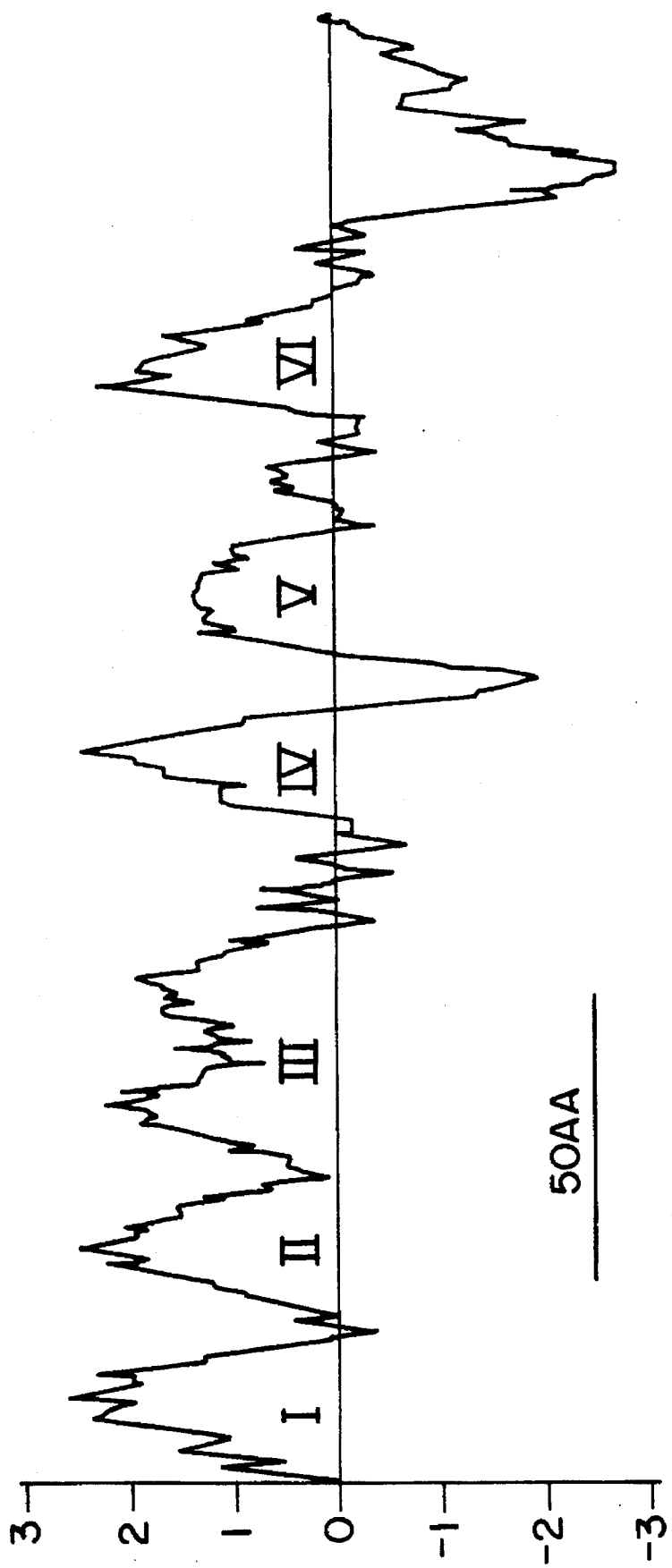
FIG. 1 is a chart illustrating a hydropathy profile of a presumed amino acid sequence of WCH-1.

FIG. 1 shows hydropathy profile of the deduced amino-acid sequence of the WCH-1. The mean hydrophobicity index was computed according to the algorithm of Kyte and Doolittle (Kyte, J. & Doolittle, R. F. J. Mol. Biol. 157, 105–132 (1982)) with a window of 12 residues. Hydropathy analysis if the translated protein indicated the presence of the six transmembrane domains similar to CHIP 28. Deduced membrane-spanning domains are numbered from I to VI.

Although the experiments have been conducted in the present invention on rats, it is apparent that the WCH-1 cDNA of any other animal species may be obtained by the above-described operations, if such animal species are mammals. It may be premeditated that substantial portions of the base sequence and the amino acid sequence exhibit identity with these other animal species. (It is noted that for instance, human CHIP 28 and rat CHIP 28 exhibited 88% base sequence identity.)

Investigation into the Presence of Tissue of WCH-1

For Northern blot analysis, RNA extracted from several tissues was enriched for poly(A)$^+$ tracts and 10 μg per lane was electrophoresed on agarose gels containing formaldehyde. Equal loading and absence of degradation was checked by staining with ethidium bromide. After transfer to nylon membranes, blots were hybridized under high stringency with the WCH-1 cDNA labeled with $^{32}$P, and autoradiographed for 24 to 120 hours.

RT-PCR of dissected nephron segments was performed as described in Moriyama, T., Murphy, H. R., Murtin, B. M. & Garcia-Perez, A. Am. J. Physiol, 258, F1470–F1474 (1990) and Terada, Y. et al. Am. J. Physiol. 261, F1080–F1087 (1991). Briefly, 2 mm of dissected nephron segments were submitted to reverse transcription (RT) with random primer. Synthesized cDNA was used for 40 cycles of PCR reaction (94° C. for 1 minute, 60° C. for 1 minute, 72° C. for 3 minutes), with specific 18nt primers for WCH-1 (5'-TGGGATCTATTTCACCGG-3' (SEQ ID NO:6), bases 522–539, and 5'-ACAGGCACTCGGGATCAC-3' (SEQ ID NO:7), bases 1216–1233).

PCR products were electrophoresed in 2% agarose, stained with ethidium bromide, and photographed. For Southern blot analysis, DNA was denatured and transferred to nylon membranes and hybridized with WCH-1 cDNA labeled with $^{32}$P.

FIG. 2 shows photographs of localization of WCH-1.

Figure 2A:
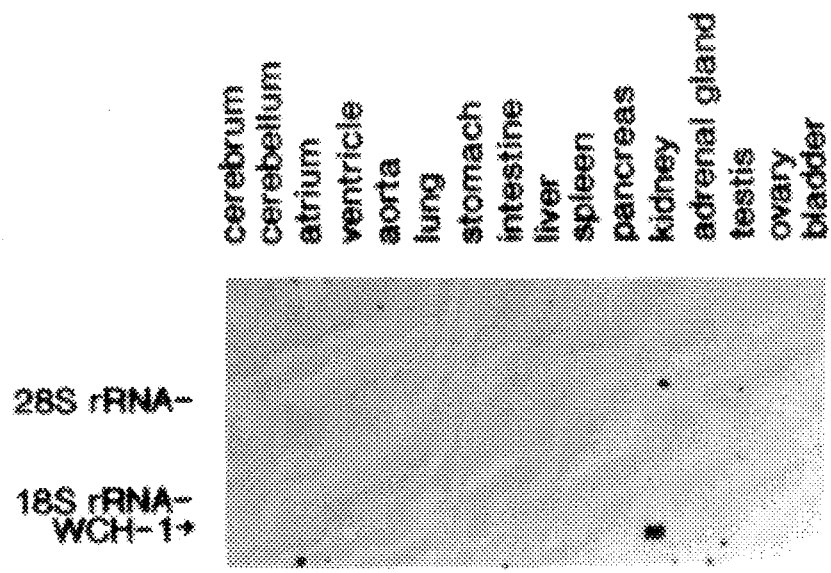
FIG. 2(a) is a photo showing results Northern blot analysis of WCH-1 in a variety of rats' tissues.

FIG. 2a shows Northern blot analysis of WCH-1 expression in different rat tissues, showing WCH-1 transcripts detected only in the lane containing rat kidney mRNA. WCH-1 transcripts were not detected in lanes other than kidney mRNA by longer autoradiographic exposure up to 120 hours (data not shown).

Figure 2B:
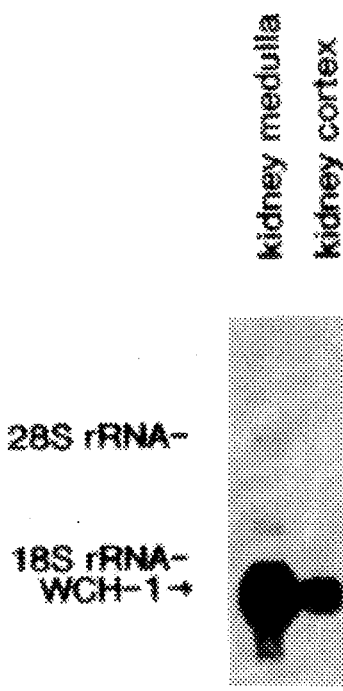
FIG. 2(b) is a photo showing results of the Northern blot analysis of WCH-1 in sliced segments of the cortex and medulla of the rat's kidney.

FIG. 2b shows Northern blot analysis of WCH-1 expression in sliced sections of rat kidney cortex and medulla. In addition to a major transcript of ~1.5 Kb, larger transcripts of 2.8 Kb and 4.4 Kb were detected. These may represent alternative splicing or polyadenylation variants.

The above northern blot analysis revealed that WCH-1 is expressed exclusively in kidney, predominantly in kidney medulla and less in kidney cortex.

Figure 3:
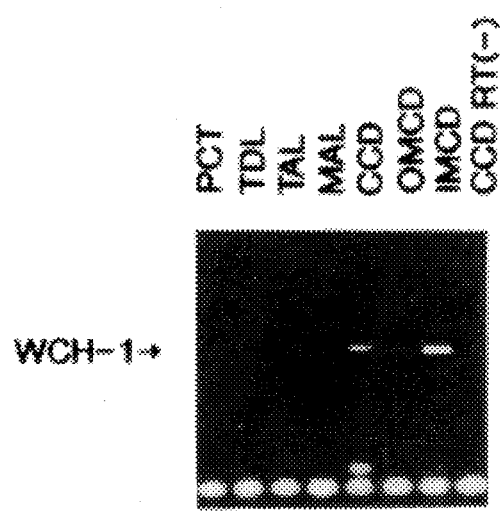
FIG. 3 is a photo showing agarose gel electrophoresis of an RT-PCR product for WCH-1 mRNA for an isolated nephron segment.

FIG. 3 shows agarose gel electrophoresis of RT-PCR products for WCH-1 mRNA on dissected nephron segments. 712 bp bands for WCH-1 were detected in lanes on CCD, OMCD, IMCD.

By Southern blot analysis, specific binding of probes to PCR bands confirmed the identity of the products (data not shown).

Abbreviations are: PCT, proximal convoluted tubule; TDL, thin descending limb of Henle's loop; TAL, thin ascending limb of Henle's loop; MAL, medullary thick ascending limb; CCD, cortical collecting tubule; OMCD, outer medullary collecting tubule; IMCD, inner medullary collecting tubule; RT (–), reaction without reverse transcriptase.

PCR products of 712 bp specific for WCH-1 was detected only in the cortical, and the outer and inner medullary collecting tubule segments, suggesting the limited expression of WCH-1 mRNA in the collecting tubule.

Then, immunohistochemical localization of WCH-1 in a rat kidney was checked. A peptide corresponding to 15 amino acids at the COOH-terminus of WCH-1 (Val-Glu-Leu-His-Ser-Pro-Gln-Ser-Leu-Pro-Arg-Gly-Ser-Lys-Ala) (SEQ ID NO:8), with the $NH_2$ terminus of tyrosine, was synthesized, and conjugated with bovine thyroglobulin in accordance with Skowsky, W. R. & Fischer, D. A. J. Lab. Clin. Med. 80, 134–144 (1972). The resulting product is termed a conjugate. Using 0.5 mL of the conjugate obtained by mixing the complete Freund's adjuvant into the conjugate (0.2 mg as peptide), a New Zealand white rabbit was immunized to obtain a rabbit anti-serum (termed anti-WCH1/C hereinafter).

4 μm sections of a fixed kidney of a rat restricted in water intake for two days were mounted on slides, pre-incubated with a non-immune goat serum, and rinsed. The slides were incubated overnight at 4° C. with 500:1 diluted anti-WCH1/C and rinsed. The rinsed slides were incubated with a 1:100 diluted solution of FITC-conjugated goat-anti-rabbit immunoglobulin at 25° C. for one hour and stained. The stained slides were rinsed and photographed (FIGS. 4 to 7). Immunostaining with anti-sera from three of five immunized rabbits (anti-WCH1/C) produced similar results.

FIG. 4 shows the rat kidney medulla portion incubated with anti-WCH1/C by the above procedure with a magnification factor of 100. FIG. 5 shows the rat kidney medulla portion incubated with anti-WCH1/C which has been pre-incubated with a corresponding peptide immunogen, with a magnification factor of 100. Specificity of the antibody staining was confirmed by the disappearance of the staining (FIG. 5), by the pre-incubation with the peptide immunogen, which staining was observed in the apical domain of the cells of the collecting tubule (FIG. 4).

FIG. 6 shows the rat's medullar portion incubated with anti-WCH-1, with a high magnification factor of 400. FIG. 7 shows the rat's kidney cortical portion incubated with anti-WCH1/C, with a magnification factor of 100.

Immunofluorescence staining was observed only in the cortical and medullar collecting tubules but not observed in other nephron segments inclusive of proximal tubule, thin descending tubule or thin ascending limb (FIG. 4 and 7). Specificity of the antibody staining was confirmed by the lack of staining of the sections when antiserum was preincubated with the corresponding peptide immunogen (FIG. 5). Immunolocalization of WCH-1 along the nephron segments, together with RT-PCR localization of WCH-1 mRNA, indicate the exclusive expression of WCH-1 in the collecting tubule, contrary to CHIP 28, which expresses itself in the proximal tubule and the descending thin limb of Henle's loop (Denker, B. M., Smith, B. L., Kuhajda, F. P. & Agre, P. J. Biol. Chem. 263, 15634–15642 (1988)).

It is known that minority of cells of the cortical collecting tubule are not stained, and that these cells are intercalated cells in which the water channels are not expressed (Handler, J. S. Am. J. Physiol. 255, F375–F382 (1988)). According to the intracellular immunochemical localization examined at high magnification, the apical membrane of the cells of the collecting tubule were stained deeply, whereas basolateral sides of the cells were hardly stained (FIG. 6). As a result thereof, it was proved that WCH-1 was localized to the apical membrane of the cells of the collecting tubule. Interestingly, staining could be observed in the sub-apical region of the cell, in addition to intense staining in the apical membrane. Although spatial resolution is not high enough, this is indicative of the presence of the water channels in the sub-apical endosomal reservoir.

Proof that WCH-1 is a Water Channel

To determine the osmic water permeability of oocytes injected with the WCH-1 transcript, volume increase caused by an imposed osmotic gradient was measured using videomicroscopy (Zhang, R. & Verkman, A. S. Am. J. Physiol. 260, C26–C34 (1991)).

Capped cRNA was synthesized from WCH-1 in pSPORT vector using T7 RNA polymerase after linearization of the pSPORT vector. Oocytes were obtained from female *Xenopus laevis* and prepared as described in Dascal, N. CRC Crit. Rev. Biochem. 22, 317–373 (1987), then injected with 20 ng of water or 20 ng of WCH-1 RNA (1 μg/μL) and incubated at 18° C. After 24 hours of incubation, oocytes were transferred from 200 mOsm Barth's buffer to 70 mOsm Barth's buffer and osmotic volume increase was observed at 24° C. by videomicroscopy (Zhang, R. & Verkman, A. S. Am. J. Physiol. 260, C26–C34 (1991)). Oocytes were viewed by light transmitted through an Olympus phase-contrast microscope and imaged on a Hamamatsu SIT camera connected to ARGUS-200 image processing system. Images were obtained and stored at 20-s intervals.

Oocytes images were processed as described in Zhang, R. & Verkman, A. S. Am. J. Physiol. 260, C26–C34 (1991) and the projection area of the oocytes was calculated by automatic summation. Relative volume ($V/V_o$) was calculated from the area at time 0 ($A_o$) and at time t (A) by:

$$V/V_o = (A/A_o)^{3/2}$$

Osmotic water permeability (Pf) was determined from an initial slope of a time curve of $V/V_o$ (d $(V/V_o)$/dt), initial oocyte volume ($V_o = 9 \times 10^{-4}$ cm$^3$), initial oocyte surface area (S=0.045 cm$^2$), the molar volume of water ($V_w = 18$ cm$^3$/mol) by:

$$Pf = [V_{oxd}(V/V_o)/dt]/[S \times V_w \times (osm_{in} - osm_{out})]$$

To examine the effects of mercurial sulfhydryl reagents, oocytes were incubated in Barth's buffer containing 0.3 mM $HgCl_2$ for 5 minutes prior to Pf measurements. The recovery of the inhibition by reducing agents was examined by 15 minutes incubation in a Barth's buffer containing 5 mM β-mercaptoethanol following 5-minute incubation in $HgCl_2$.

FIG. 8 shows an increase in osmotic water permeability of WCH-1 RNA-injected Xenopus oocytes. FIG. 8 a shows time-dependent volume increase of oocytes injected with 20 ng WCH-1 RNA (WCH-1) and with water (Control). FIG. 8b shows microphotographs of oocytes injected with WCH-1 RNA or with water (Control). Photos were taken in 20 s intervals, shown in the order of left-to-right and top-to-bottom.

Osmotic water permeability (Pf) was $25.1 \pm 1.7$ (mean±SEM)×$10^{-4}$ cm/s in oocytes injected with water and $83.9 \pm 18.2 \times 10^{-4}$ cm/s in oocytes injected with WCH-1. The osmotic water permeability coefficient (Pf) in WCH-1-injected oocytes was 3.5 times greater than Pf in water-injected oocytes.

Moreover, ten out of eleven oocytes injected with WCH-1 transcripts ruptured within 10 minutes after transfer into the hypotonic solution, whereas none of water-injected oocytes ruptured for more than 60 minutes.

The Pf value in the oocytes injected with WCH-1, which was $83.9 \pm 18.2 \times 10^{-4}$ cm/sec, was lowered to $44.5 \pm 3.6 \times 10^{-4}$ cm/sec after incubation for five minutes in 0.3 mM of $HgCl_2$, due to partial suppression of activity of the WCH-1 water channel. Suppression by $HgCl_2$ was recovered by incubation in 5 mM B-mercaptoethanol for 15 minutes following incubation in 0.3 mM of $HgCl_2$ (Pf=63.1±25.8×10$^{-4}$ cm/sec).

The activation energy (Ea) for osmotic water permeability of oocytes injected with WCH-1 cRNA, estimated from the Arrhenius Plot of Pf measured at 10° to 28° C. was 3.6±0.8 kcal/mol (n=12), which is comparable to those reported for water channels in RBC and kidney proximal and collecting tubules (Verkman, A. S. Annu. Rev. Physiol. 54, 97–108 (1992)).

Appearance of high osmotic water permeability, and low activation energy, together with the inhibition by mercurial reagents acting on sulfhydryl groups and the recovery with reducing agents, which are characteristic to channel mediated water permeability (Verkman, A. S. Annu. Rev. Physiol. 54, 97–108 (1992)), strongly suggest that the expressed protein in the WCH-1-injected oocytes is a water channel.

Our observed Pf value in WCH-1-injected oocytes was lower than that reported for CHIP 28-injected oocytes. Possible explanations for it include reduced translation of WCH-1 protein without using a Xenopus β-globin chimaeric vector (Preston, G. M., Carroll, T. P. Guggino, W. B. & Agre, P. Science 256, 385–387 (1992)), and reduced surface expression of WCH-1 in oocytes due to the lack of the vasopressin-regulated membrane trafficking mechanisms, which are necessary for translocating water channels from subapical reservoir vesicles to the apical membrane (Handler, J. S. Am. J. Physiol. 255, F375–F382 (1988)). Also, in Xenopus oocytes, endosomal water channel protein could only partially be expressed in the plasma membrane because of the non-specific targetting of foreign protein in the egg (Dascal, N. CRC Crit. Rev. Biochem. 22, 317–373 (1987); Sigel, E. J. Membrane Biol. 117, 201–221 (1990)).

To examine the effects of water deprivation, 50 µg of RNA from rat whole kidney after 0, 2, and 5 day of water restriction were used. RNA was size fractionated by agarose-formaldehyde gel electrophoresis. Equal loading and absence of degradation were checked by staining with ethidium bromide and by hybridization with $^{32}$P-labeled β-actin. After transfer to nylon membranes, blots were hybridized under high stringency with the WCH-1 cDNA for WCH-1 expression and the insert of prCHIP 28 for CHIP 28 expression labeled with $^{32}$P, and autoradiographed.

FIG. 9 shows the results of Northern blot analysis of the regulation of WCH-1 and CHIP 28 mRNA abundance after prolonged water deprivation in Rat kidney.

Significant induction of WCH-1 mRNA, but not of CHIP 28 mRNA, in rat kidney after prolonged water deprivation suggests that during prolonged antidiuresis, an increment in collecting tubule water channel protein may contribute to the increase in water permeability.

The antidiuretic action of vasopressin includes rapid increases in water permeability of the collecting tubule by inserting water channels into the apical membrane (Ganote, C. E. et al. J. Cell Biol. 36, 355–367 (1968); Kuwahara, M., Berry. C. A. & Verkman. A. S. Biophys. J. 54, 595–602 (1988); Verkman, A. S. Annu. Rev. Physiol. 54, 97–108 (1992)), and an increased urinary concentration capacity by amplifying the countercurrent multiplication system and the corticomedullary osmolality gradient (Knepper, M. A. & Rector, F. C. Jr. in the Kidney (eds Brenner, B. M. & Rector, F. C. Jr.) 445–482 (W. B. Saunders, Philadelphia, 1991); Kirk, K. L. & Schafer, J. A. in the Kidney: Physiologh and Pathophysiology (eds Seldin, D. W. & Giebisch, G.) 1693–1725 (Raven Press, New York, 1992)).

Our results indicate the possibility that vasopressin may also increase maximal water permeability by increasing the synthesis of water channels in the collecting tubule.

Because vasopressin causes enormous increase in osmotic water permeability of the apical membrane of the collecting tubule from basal level, comparable to that of other biological membranes that do not contain water channels (Verkman, A. S. Annu. Rev. Physiol. 54, 97–108 (1992); Kuwahara, M., Berry. C. A. & Verkman. A. S. Biophys. J. 54, 595–602 (1988)), all or at least the majority of water channels in the apical membrane are considered to be vasopressin regulated. The presence of WCH-1 exclusively in the apical domain of the collecting tubule cells, and the functional expression of water channel in oocytes strongly indicate that WCH-1 is indeed the vasopressin-regulated water channel of the apical and endosomal membranes of the collecting tubule.

Molecular identification of the apical membrane water channel will enable direct investigation on the cellular mechanisms of the vasopressin-regulated water permeability of the collecting tubule cells.

Means for Obtaining WCH-1 Protein

Cyclic plasmid pSPORT is sectioned with restrictive enzymes Not-I and Sal-I, and WCH-1 cDNA is inserted into the sectioned sites. The plasmid into which WCH-1 gene has been recombined is introduced into an *Escherichia coli* DH10α strain for transformation.

The transformation of host by the recombinant DNA may be realized by a known method (Cohen, S. N. et al., Proc. Natl. Acad. Sci., USA., 69, 2110 (1972)) or a similar method.

The produced transformant or recombinant is cultivated on a known medium, such as (ampicillin-containing) L-broth medium. IPTG is added during cultivation in order for the promotor to be operated more effectively during a certain predetermined period following bacterial proliferation. After IPTG addition, cultivation is continued usually for 3 to 4 hours at 37° C. After the cultivation, bacteria are collected by any known method, suspended in a buffer solution and raptured. WCH-1 protein is purified by any known method, such as column chromatography.

EXAMPLES OF INDUSTRIAL UTILIZATION

The following industrial advantages may be accrued by the isolation, identification and cloning of WCH-1 which are enabled by the present invention.

A screening method for water diuretics utilizing a substance in which the WCH-1 protein is expressed, such as following screening methods for water diuretics, may be established.

1) Several peptides thought to be the center of activity may be artificially synthesized from the amino acid sequence of WCH-1, and substances which are specifically linked to these peptides are screened.

2) A large quantity of WCH-1 protein is produced from the *Escherichia coli* having the WCH-1 recombinant plasmid according to the present invention and substances which are specifically linked to such protein are screened.

3) mRNA artificially produced from WCH-1 cDNA is injected into eggs of Xenopus to express WCH-1 protein on the egg membrane. Since the eggs are dilated on lowering of the osmotic pressure of the external liquid, the eggs are cultivated in a hypotonic liquid and the dilation is monitored to screen substances which are restrained in dilation.

4) An antibody against the extracellular domain of the WCH-1 protein is prepared, and substances which inhibit combination of the antibody with the WCH-1 protein are screened.

5) A vector in which WCH-1 cDNA is incorporated is transplanted on a suitable culture cell, such as COS-7 cell. Since the transplanted cell is improved in water permeability, water flows into the cell to be dilated and exploded on decreasing the osmotic pressure of the external liquid. Therefore, substances which restrict such explosion are screened.

An artificial membrane in which the WCH-1 protein is incorporated (Bear, C. E. et al., Cell, 68, 809–818 (1992)) exhibits high water permeability and may be used in a number of ways. For example, 1) The artificial membrane may be used as a membrane for ultrafiltration for preparation of pure water.
2) It may be used for salt concentration.
3) It may be used as an osmotic pressure sensor.
4) It may also be used for screening of water diuretics.

Above all, the WCH-1 protein incorporated into liposome as a type of the lipid membrane may also be used in a variety of ways. For example, 1) it may be designed as artificial blood cells:
2) it may be designed as the above-mentioned liposome into which pharmaceuticals are contained. Such liposome is suitable as a durable slow-release pharmaceuticals because of retarded release of the pharmaceuticals in the blood;
3) it may be used as a therapeutic drug for patients showing resistivity to water diuretics and for patients suffering from severe edema.

If liposome containing high osmotic pressure substances is ingested, body water is captured into liposome and ultimately excreted as feces, in other words, water discharge into feces is promoted.

4) The liposome may be used as a water absorbant.

The liposome containing high osmotic pressure substances exhibit high water absorption properties. Therefore, if a large quantity of the liposome are filled between paper cells of a paper product, such paper product is markedly improved in water adsorptive properties, and hence may be used as a diaper or a sanitary napkin.

The liposome into which WCH-1 protein is incorporated may be produced by any of known methods. Among the common methods, there are a freezing melting method (M. Kasahara, P. C. Hinkle, J. Biol. Chem., 252, 7384 (1977)), a dilution method by octylglucoside (M. J. Newman, T. H. Wilson, J. Biol. Chem., 255, 10583 (1980)) and a dialysis method (Y. Kagawa, A. Kandrach, E. Racker, J. Biol. Chem., 248, 676 (1973)).

The size and properties (i.e. single- or multi-layered) of the liposome are suitably selected depending on lipid types.

As an example, the WCH-1 protein, the lipid (preferably as a mixture with phospholipid) and a surfactant (e.g. deoxycholate) are mixed together and agitated ultrasonically. The surfactant is removed by dialysis or gel filtration to produce liposome into which is incorporated the WCH-1 protein.

An example of liposome preparation by the freezing and melting method is explained.

Preparation Example

To 100 mM of tris-hydrochloric acid buffer solution (pH 7.5), 50 mM of $MgCl_2$ and 22.5 mg of azolectin (crude lipid of soybeans) processed with acetone are added 0.5 mL of a 10 mM tris-hydrochloric acid buffer solution (pH 7.5). After blowing a nitrogen gas into the resulting mixture, the mixture is treated for about 20 minutes by a water-bath type ultrasonic vibrator by ultrasonic waves until the mixture is substantially transparent.

167 µL of this liposome, 20 µg of purified WCH-1 protein and 10 mM of tris-hydrochloric acid buffer solution (pH 7.5) are combined to an overall volume of 0.5 mL. After blowing nitrogen gas into the resulting mass, the mass is frozen in acetone cooled to $-70°$ C. After melting at room temperature, the melted mass is ultrasonically treated for 15 sec using a water-bath type ultrasonic vibrator. The so-treated mass is diluted with 50 mM $MgCl_2$–100 mM tris-hydrochloric acid buffer solution (pH 7.5) and water to produce liposomes in which WCH-1 protein is incorporated in the form of 8 mg lipid in 1 mL of 2 mM $MgCl_2$–10 mM tris-hydrochloric acid buffer solution.

On the other hand, since it now becomes possible to duplicate the WCH-1 cDNA according to the present invention and to synthesize WCH-1 mRNA artificially, it becomes possible to express the WCH-1 protein on a living membrane by employing a known technique as disclosed in M. Mishina et al., Nature (London), 307, 604 (1984).

For example, the WCH-1 protein may be expressed on the cell membrane by transplanting the plasmid in which WCH-1 cDNA is incorporated on the cell medium or by injecting WCH-1 mRNA into oocytes, as shown in the above exemplification.

It should be noted that modifications apparent in the art may be done without departing from the present invention within the gist and scope of the present invention as herein disclosed and claimed.

Appendix:

Table of Sequence Description

---

What is claimed is:

1. A WCH-1 DNA in isolated and purified form which is complementary to rat mRNA that encodes a vasopressin-regulated water channel protein localized in the kidney collecting tubule.

2. A purified and isolated mammalian WCH-1 protein molecule.

3. The WCH-1 protein molecule of claim 2 having an amino acid sequence encoded by the nucleotide sequence of SEQ ID NO:3.

4. A recombinant plasmid comprising an expression system that expresses a nucleotide sequence which encodes the protein of claim 2.

5. The recombinant plasmid of claim 4 comprising the expression vector pSPORT.

6. A recombinant host cell that produces a WCH-1 protein molecule constituting a vasopressin-regulated water channel localized in the kidney collecting tubule, which recombinant host cell is modified to contain the recombinant plasmid of claim 4.

7. The recombinant host cell of claim 6 which is an *Escherichia coli*.

8. The recombinant host cell of claim 7 wherein said WCH-1 protein is encoded by the nucleotide sequence of SEQ ID NO:3.

9. The recombinant host cell of claim 6 which is obtained by introducing a recombinant plasmid capable of expressing the WCH-1 gene into *Escherichia coli* DH10α.

10. A method to produce a WCH-1 protein which method comprises culturing the recombinant host cells of claim 6 under conditions which favor expression of said WCH-1 protein; and recovering the WCH-1 protein from the culture.

11. A WCH-1 protein produced by the method of claim 10.

12. An isolated DNA molecule encoding the amino acid sequence of a mammalian WCH-1 protein wherein said protein is encoded by a mammalian mRNA that encodes a vasopressin-regulated water channel protein localized in the kidney collecting tubule.

13. The DNA molecule of claim 12 encoding the rat WCH-1 protein having the amino acid sequence encoded by the nucleotide sequence of SEQ ID NO:3.

14. The recombinant plasmid of claim 4 that expresses a nucleotide sequence encoding a protein encoded by the nucleotide sequence of SEQ ID NO:3.

15. The method of claim 10 wherein said WCH-1 protein is encoded by the nucleotide sequence of SEQ ID NO:3.

16. The WCH-1 protein of claim 11 which is encoded by the nucleotide sequence of SEQ ID NO:3.

\* \* \* \* \*